United States Patent [19]

Celmer et al.

[11] 4,148,883

[45] Apr. 10, 1979

[54] ANTIBIOTICS PRODUCED BY NEW SPECIES OF NOCARDIA

[75] Inventors: Walter D. Celmer, New London; Walter P. Cullen, East Lyme; Charles E. Moppett, Mystic; Mark T. Jefferson, Waterford; Liang H. Huang, East Lyme, all of Conn.; Riichiro Shibakawa, Handa; Junsuki Tone, Chita, both of Japan

[73] Assignee: Pfizer Inc., New York, N.Y.

[21] Appl. No.: 825,563

[22] Filed: Aug. 18, 1977

[51] Int. Cl.$^2$ .............................................. A61K 35/00
[52] U.S. Cl. .................................... 424/122; 424/115
[58] Field of Search ................... 424/122, 115; 195/81

[56] References Cited

U.S. PATENT DOCUMENTS 4,038,383   7/1977   Celmer et al. ...................... 424/119

Primary Examiner—Jerome D. Goldberg
Attorney, Agent, or Firm—Connolly and Hutz

[57] ABSTRACT

A new species of Nocardia, designated *Nocardia argentinensis* Huang sp. nov., when subjected to aerobic submerged fermentation, produces a mixture of new antibiotics. Methods for the recovery and purification of these antibiotics are described and some of their antimicrobial properties are outlined.

3 Claims, 1 Drawing Figure

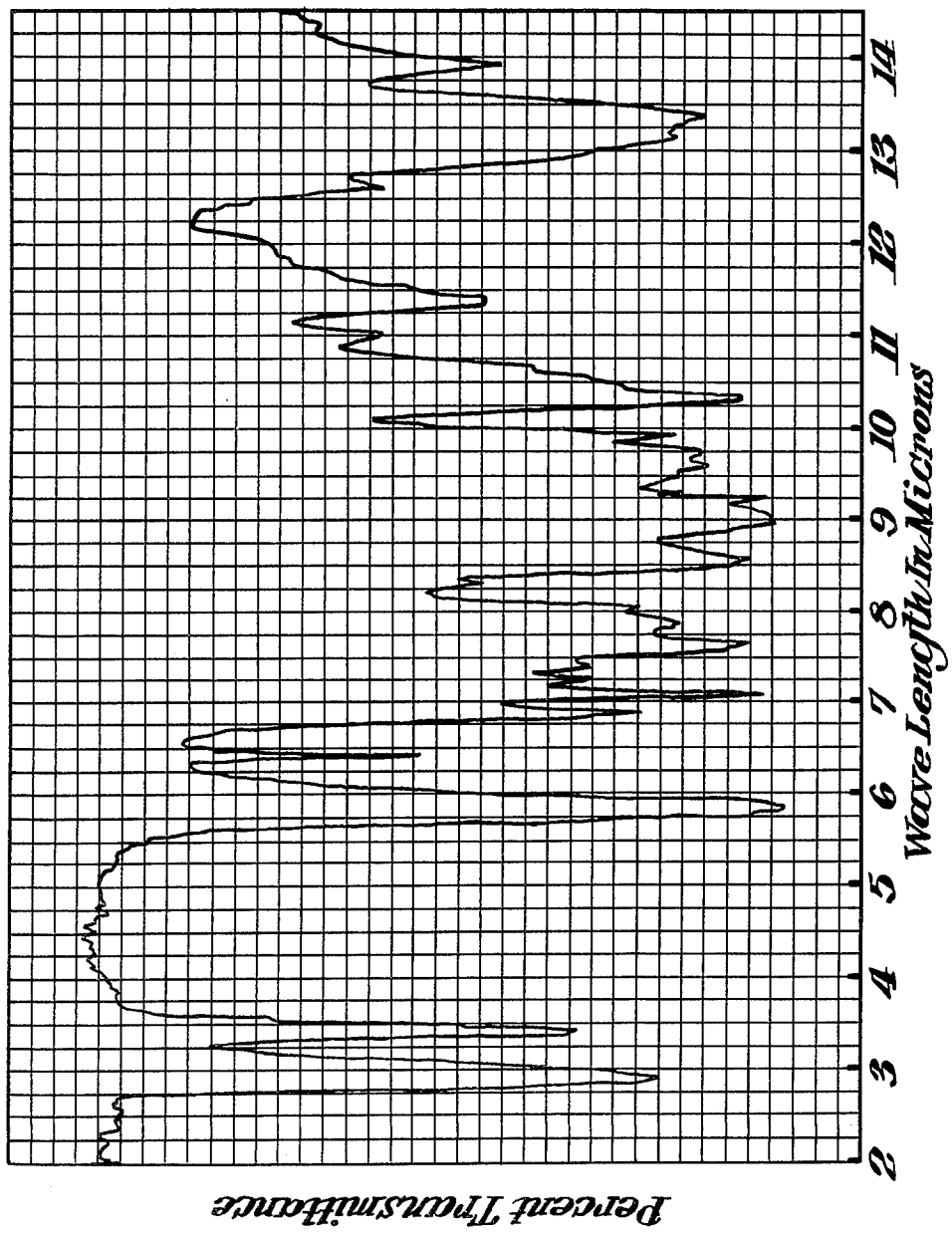

ANTIBIOTICS PRODUCED BY NEW SPECIES OF NOCARDIA

BACKGROUND OF THE INVENTION

The search for new antibiotics produced by soil microorganisms has encompassed the screening of various genera of bacteria, and fungi including many species within each genus and many strains within each species.

Among the microorganisms that have received somewhat less attention than others are those that belong to the genus Nocardia. This genus has the narrow hyphae of the Actinomycetales and is characterized by fragmentary substrate mycelium. The generic identity may be further supported by a cell wall of type IV as described by H. A. Lechevalier and M. P. Lechevalier, A Critical Evaluation of the Genera of Aerobic Actinomycetes, pages 393–405, in The Actinomycetales (1970), edited by H. Prauser and published by Fischer, Jena. This genus is further characterized by a whole-cell sugar pattern of type A as described by M. P. Lechevalier, Identification of Aerobic Actinomycetes of Clinical Importance, J. Lab. Clin. Med., 71(6), 934–944 (1968).

SUMMARY OF THE INVENTION

This invention is concerned with Compounds 47,444, 47,985 and 48,039, antibiotics produced under submerged aerobic fermentation conditions by *Nocardia argentinensis* Huang sp. nov. ATCC 31306.

DETAILED DESCRIPTION OF THE INVENTION

The microorganism useful for the preparation of the antibiotics of this invention was isolated from a soil sample from Argentina. This culture (Pfizer F. D. 25952), designated *Nocardia argentinensis* Huang sp. nov., has been deposited in The American Type Culture Collection, Rockville, Md. as the type culture under their accession number ATCC 31306. The permanency of the deposit and ready accessibility thereto by the public are afforded in the event the patent is granted. Access to the culture is available during pendency of the application under Rule 14 and 35 USC 112. All restrictions on the availability to the public of the culture deposited will be irrevocably removed upon granting of the patent.

The culture was planted from a 5-day-old-slant into liquid ATCC No. 172 medium and grown for 3 days at 28° C. on a shaker. It was then homogenized for 30 seconds in a blender, centrifuged for 20 minutes, washed three times with sterile distilled water and planted on media commonly used for identification of members of the Actinomycetales.

The inoculated media were incubated at 28° C. and records of results were made after suitable incubation time with most final results recorded at a period of 13 days. The colors were described in common terminology, but exact color was determined by comparison with color chips from the Color Harmony Manual, fourth edition. About 20 grams of washed, autoclaved mycelium of the culture were used for cell wall analyses.

Identification media used for the characterization of the culture and references for their composition are as follows.

1. Tryptone Yeast Extract Broth (ISP #1 medium, Difco).
2. Yeast Extract—Malt Extract Agar (ISP #2 medium, Difco).
3. Oatmeal Agar (ISP #3 medium, Difco).
4. Inorganic Salts—Starch Agar (ISP #4 medium, Difco).
5. Glycerol—Asparagine Agar (ISP #5 medium, Difco).
6. Peptone—Yeast Extract Iron Agar (ISP #6 medium, Difco).
7. Tyrosine Agar (ISP #7 medium, Difco).
8. Gelatin—R. E. Gordon and J. M. Mihm, Jr. Bact. 73:15–27, 1957.
9. Starch—Ibid.
10. Organic Nitrate Broth—Ibid.
11. Dextrose Nitrate Broth—S. A. Waksman, The Actinomycetes, Vol. 2, medium no. 1, p. 328, 1961, with 3 g dextrose substituted for 30 g sucrose and agar omitted.
12. Potato Carrot Agar—M. P. Lechevalier, Jr. Lab. and Clinical Med. 71:934–944, 1968 but use only 30 g potatoes, 2.5 g carrots and 20 g agar.
13. 2% Tap Water Agar.
14. Czapek-Sucrose Agar—S. A. Waksman, The Actinomycetes, Vol. 2, medium no. 1, p. 328, 1961.
15. Glucose Asparagine Agar—Ibid, medium no. 2, p. 328.
16. Glucose-Yeast Extract Agar—Ibid, medium no. 29, p. 331.
17. Emerson's Agar—Ibid, medium no. 28, p. 331.
18. Nutrient Agar—Ibid, medium no. 14, p. 330.
19. Potato Dextrose Agar—J. N. Couch, Jr. Elisha Mitchell Soc. 79:53–70, 1963.
20. Gordon and Smith, Tyrosine Agar—R. E. Gordon and M. M. Smith, Jr. Bact. 69:147–150, 1955.
21. Casein Agar—Ibid.
22. Calcium Malate Agar—S. A. Waksman, Bact. Rev. 21:1–29, 1957.
23. Skim Milk—Difco.
24. Cellulose utilization—
   (a) H. L. Jensen, Proc. Linn. Soc. N.S.W. 55:231–248, 1930.
   (b) M. Levine and H. W. Schoenlein, A Compilation of Culture Media, medium 2511, 1930.
25. Carbohydrates—G. M. Luedemann and B. C. Brodsky, Antimicrobial Agents and Chemotherapy, 1964:47, 1965.
26. Temperature Range—ATCC medium 172 in ATCC Culture Collection Catalogue, 12th. ed. p. 329, 1976.

The culture, *Nocardia argentinensis* Huang sp. nov., was described as follows on the various culture media:

Yeast Extract-Malt Extract Agar—Growth good, white but pale orange (4 ga) near ends of streak, smooth to wrinkled, with white aerial mycelium; reverse pale orange (3 ga); no soluble pigment.

Oatmeal Agar—Growth moderate to good, white, thin, smooth, with white aerial mycelium; reverse colorless; no soluble pigment.

Inorganic Salts-Starch Agar—Growth poor to moderate, white, thin, smooth, with scant white aerial mycelium; reverse colorless; no soluble pigment.

Glycerol-Asparagine Agar—Growth moderate, white, thin, smooth, with white aerial mycelium; reverse pale orange (3 ea); no soluble pigment.

Gelatin—Growth good, white, slightly raised, smooth, with white aerial mycelium; reverse yellowish orange (3 ia); no soluble pigment.

Starch—Growth good, white, slightly raised, smooth, with white aerial mycelium; reverse pale yellowish (3 ga); no soluble pigment.

Potato Carrot Agar—Growth moderate, white with pale orange tint (near 3 ca), thin, smooth; reverse pale orange (3 ea to 3 ga); no soluble pigment.

Tap Water Agar—Growth poor, white, thin, smooth, with scant white aerial mycelium; reverse colorless to very pale orange (3 ca); no soluble pigment.

Czapek-Sucrose Agar—Growth poor to moderate, white, thin, smooth, with white aerial mycelium; reverse pale orange (3 ca); no soluble pigment.

Glucose Asparagine Agar—Growth good, white with small orange dots (4 ea), slightly raised and roughened, with white aerial mycelium; reverse yellowish orange (3 ga); no soluble pigment.

Glucose-Yeast Extract Agar—Growth good, white but orange (4 ga) at ends of streak, raised, wrinkled; reverse orange (4 la); pale yellowish soluble pigment.

Emerson's Agar—Growth good, orange (4 ea to 4 ia), raised, wrinkled, with short white aerial mycelium; reverse orange (4 la); no soluble pigment.

Nutrient Agar—Growth moderate, white, thin, smooth, with white aerial mycelium; reverse pale orange (3 ea); no soluble pigment.

Potato Dextrose Agar—Growth good, white with yellowish orange dots (3 ga to 3 ia), raised, slightly roughened with white aerial mycelium; reverse yellowish orange (3 ia); no soluble pigment.

Gordon and Smith' Tyrosine Agar—Growth moderate to good, white with very pale orange tint, thin, smooth with many small raised dots, aerial mycelium white; reverse like surface; soluble pigment brown (6 pn).

Casein Agar—Growth good, white, slightly raised, smooth but slightly wrinkled at the edge of streak, aerial mycelium white; reverse colorless; soluble pigment yellowish brown (3 lc).

Calcium Malate Agar—Growth poor to moderate, white, thin, smooth but granular in some areas, with white aerial mycelium; reverse very pale orange (3 ca); no soluble pigment.

Biochemical Properties—Gram-positive; non-acid-fast; no melanin; hydrogen sulfide not produced; gelatin liquefied; starch not hydrolyzed; nitrate reduced to nitrite; no disintegration on both Jensen's cellulose and Levine and Schoenlein's cellulose; clearing but no coagulation on milk; casein digestion positive; tyrosine digestion positive; no digestion of calcium malate; no decomposition of xanthine; decomposition of hypoxanthine positive. Carbohydrate utilization: glucose, inositol, glycerol, mannose, ribose, and trehalose utilized; arabinose, fructose, raffinose, sucrose, xylose and melibiose doubtfully utilized; mannitol, rhamnose, adonitol, cellobiose, dulcitol, galactose, lactose, melezitose, salicin, sorbitol, sorbose and starch not utilized.

Morphological Properties—Morphological observations were made 8 hr, 24 hr, 5 da, 18 da, and 24 da after incubation of the culture on Czapek-Sucrose agar: Microcolonies consisting of an extensively branched substrate mycelium which begin to fragment into bacillary and coccoid cells after 24 hr incubation; fragmented cells rod-shaped or globose, smooth, measuring 0.8–1.0 μm or 1-2(-3)×0.6–0.9 μm; aerial mycelium sparse, short, often zig-zagged, may fragment into bacillary and coccoid cells as the culture ages.

| Temperature Relations | | | |
|---|---|---|---|
| 21° C. | 28° | 37° | 45° |
| Excellent Growth | Good to Excellent Growth | Good Growth | No Growth |

The culture was gram-positive, non-acid-fast, and was characterized by the fragmentation of substrate mycelium after 24 hr of incubation, the white aerial mycelium and the pale orange substrate mycelium. The cell wall had meso-diaminopimelic acid, arabinose, galactose, and mycolate of the nocardomycolate type characteristic of the species of Nocardia. It could not be identified with any known species of Nocardia and hereby described as new under the name *Nocardia argentinensis* Huang sp. nov. The specific epithet refers to Argentina where the soil sample yielding the culture was collected.

Cultivation of *Nocardia argentinensis* preferably takes place in aqueous nutrient media at a temperature of 24°–36° C. and under submerged aerobic conditions with agitation. Nutrient media which are useful for such purposes include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles and yeast extract as well as salts such as sodium chloride and calcium carbonate and trace elements such as iron, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the organism and throughout its growth.

Inoculum for the preparation of the antibiotic may be obtained by employing growth from a slant of the culture. The growth may be used to inoculate either shake flasks or inoculum tanks or the inoculum tanks may be seeded from the shake flasks. Growth in shaken flasks will generally have reached its maximum in 2 to 4 days whereas inoculum in submerged inoculum tanks will usually be at the most favorable period in 1.5–3 days. Substantial antibiotic activity is obtained in the final fermentor stage in approximately 2 to 5 days.

The process of antibiotic production is conveniently followed during fermentation by biological assay of the broth employing a sensitive strain of *Staphylococcus aureus* or *Micrococcus luteus*. Standard plate assay technique is employed in which the zone of inhibition surrounding a filter paper disc saturated with broth is used as a measure of antibiotic potency.

Thin-layer chromatography employing silica gel is a useful tool for analyzing the antibiotics produced by *Nocardia argentinensis* in fermentation media and the composition of crude and purified materials extracted from fermentation broths. Silica gel plates are employed with a developing system of chloroform:acetone (3:1 v/v). These antibiotics may be visualized by exposure to 254 nm light or bio-overlay with a thin layer of agar seeded with a sensitive strain of *Staphylococcus aureus* or *Micrococcus luteus*.

The antibiotics may be separated and recovered by extracting the whole, unfiltered fermentation broth with an organic solvent such as chloroform, ethyl acetate, methylisobutyl ketone or butanol at a pH range of 4.0 to 10.0. The solvent is concentrated to a thin syrup, defatted with heptane and chromatographed in chloroform on silica gel.

A method of separation and recovery of antibiotics 47,444, 47,985 and 48,039 is as follows: Whole fermentation broth is extracted with about ⅓ volume of methylisobutyl ketone followed by concentration in vacuo. The oily extract is triturated several times with heptane. The viscous concentrate is dispersed on silica gel in the presence of heptane and then added to a sintered glass filter coated with silica gel. The silica gel is washed successively with heptane, chloroform, varying ratios of chloroform:ethyl acetate and finally ethyl acetate. All steps in the purification sequence are monitored by thin-layer chromatography. The appropriate column cuts are pooled, preferably treated with activated charcoal and re-chromatographed on silica gel eluting with chloroform:ethyl acetate (1:1 v/v).

The present invention includes within its scope the dilute forms and crude concentrates of the mixture of antibiotics and the purified antibiotic Compound 47,444. The minor antibiotics Compound 47,985 and Compound 48,039 are present in such small amounts that it has not proved possible to isolate them in a state of homogeneity at the present time. All of these products are useful in combatting microorganisms, especially strains of *Staphylococcus aureus* that are resistant to other antibiotics.

Table I illustrates the antibacterial spectrum of Compound 47,444. These tests were run by preparing tubes of nutrient broth with gradually increasing concentrations of the pure antibiotic and then seeding the broths with the particular organism specified. The minimal inhibitory concentration indicated in Table I is the minimal concentration of the antibiotic (in micrograms/ml) at which the microorganism failed to grow. The tests were conducted under standardized conditions as described in Proc. Soc. Exp. Biol. & Med., 122, 1107 (1966).

Table I

| Organism | | Compound 47,444 (mcg/ml) |
|---|---|---|
| *Staphylococcus aureus* | 01A005 | < 0.10 |
| | 01A052 | < 0.10 |
| | 01A109 R | 0.20 |
| | 01A110 R | 0.20 |
| | 01B111 R | 0.39 |
| | 01B087 RR | 0.78 |
| | 01A400 R | < 0.10 |
| *Streptococcus faecalis* | 02A006 | 200 |
| *Streptococcus pyogenes* | 02C203 | 50 |
| | 02C020 R | 25 |
| *Mycobacterium smegmatis* | 05A001 | 200 |
| *Bacillus subtilis* | 06A001 | 1.56 |
| *Escherichia coli* | 51A229 | > 200 |
| | 51A266 | " |
| | 51A125 R | " |
| *Pseudomonas aeruginosa* | 52A104 | > 200 |
| *Klebsiella pneumoniae* | 53A009 | > 200 |
| | 53A031 R | " |
| *Proteus mirabilis* | 57C064 | > 200 |

Table I-continued

| Organism | | Compound 47,444 (mcg/ml) |
|---|---|---|
| *Proteus morganii* | 57G001 | > 200 |
| *Salmonella cholerae-suis* | 58B242 | > 200 |
| *Salmonella typhimurium* | 58D009 | > 200 |
| | 58D013 C | |
| *Pasteurella multocida* | 59A001 | 25 |
| *Serratia marcescens* | 63A017 | > 200 |
| *Enterobacter aerogenes* | 67A040 | > 200 |
| *Enterobacter cloacae* | 67B003 | > 200 |
| *Neisseria sicca* | 66C000 | 25 |

In vivo protection afforded by Compound 47,444 against mice experimentally infected with *Staphylococcus aureus* 01A005 is shown in Table II.

Table II

| Compound 47,444 | Dose (mg/kg) | Protection (%) | |
|---|---|---|---|
| | | Oral | Subcutaneous |
| | 200 | 70–90 | |
| | 100 | 50–80 | |
| | 50 | 40–50 | 50–60 |
| | 12.5 | | 20 |
| | 3.12 | | 0 |

Antibiotic Compound 47,444 can be administered via the oral or parenteral routes for the treatment in animals, including humans, of staphylococcal and other antibiotic-sensitive infections. In general, the antibiotic is most desirably administered in daily oral doses of 0.5 to 1 gram or parenteral injections of 100 to 500 mg., depending on the type and severity of the infection and weight of the subject being treated.

Antibiotic Compound 47,444 may be administered alone or in combination with pharmaceutically-acceptable carriers, and such administration can be carried out in both single and multiple doses.

For purposes of oral administration, tablets containing various excipients such as sodium citrate, calcium carbonate and dicalcium phosphate may be employed along with various disintegrants such as starch, alginic acid and certain complex silicates together with binding agents such as polyvinylpyrrolidone, sucrose, gelatin and gum acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials include lactose as well as high molecular weight polyethylene glycols. When aqueous suspension and/or elixirs are desired for oral administration, the essential active ingredient therein may be combined with various sweetening or flavoring agents, coloring matter or dyes, and if desired, emulsifying and/or suspending agents as well, together with such diluents as water, ethanol, propylene glycol, glycerol and various combinations thereof.

For purposes of parental administration, solutions of Compound 47,444 or solutions of a mixture of Compounds 47,444, 47,985 and 48,039 in sesame or peanut oil or in aqueous propylene glycol may be employed.

EXAMPLE I

A sterile aqueous medium having the following composition was prepared:

| Ingredient | Grams/liter |
| --- | --- |
| Glucose | 10 |
| Soluble starch | 20 |
| Yeast extract | 5 |
| Enzymatic digest of casein | 5 |
| Dipotassium hydrogen phosphate | 0.5 |
| Meat meal | 5 |
| Cobalt chloride | 0.002 |
| Calcium carbonate | 4 |
| pH 7.1–7.2 | |

Cells from a slant culture of *Nocardia argentinensis* ATCC 31306 were transferred to each of a number of 300 ml shake flasks each containing 40 ml of the above medium and shaken at 28° C. for three to four days.

A sterile aqueous medium having the following composition was prepared:

| Ingredient | Grams/liter |
| --- | --- |
| Glucose | 1.0 |
| Enzymatic digest of casein | 2.5 |
| Soluble starch | 5.0 |
| Corn steep liquor | 5.0 ml |
| Calcium carbonate | 3.0 |
| Cobalt chloride | 0.002 |
| pH 6.9–7.0 | |

Fermentors containing two liters of the above described sterile medium were seeded with 2–4% v/v of grown inoculum. The temperature was maintained at 30° C. The broth was stirred at 1700 r.p.m. and aerated at the rate of about one volume of air per volume of broth per minute. When substantial antibiotic activity was obtained (based on antibiotic disc assay), ca. 2–5 days, the filtered or whole fermentation broth was twice extracted with ⅓ to ½ volume of methylisobutyl ketone. The solvent was separated from the aqueous phase and concentrated in vacuo to a viscous oil.

EXAMPLE II

The fermentation process of Example I may be repeated employing the following fermentation medium:

| Ingredient | Grams/liter |
| --- | --- |
| Dextrin | 20 |
| Soybean flour | 10 |
| Distiller's solubles | 1 |
| Ferrous sulfate | 0.1 |
| pH 6.9–7.1 | |

EXAMPLE III

The fermentation process of Example I may be repeated employing the following fermentation medium:

| Ingredient | Grams/liter |
| --- | --- |
| Glucose | 10 |
| Soluble starch | 20 |
| Yeast extract | 5 |
| Enzymatic digest of casein | 5 |
| Calcium carbonate | 1 |
| Cobalt chloride | 0.002 |
| pH 6.9–7.1 | |

EXAMPLE IV

The fermentation process of Example I was repeated. About 0.1% of the grown inoculum was used to inoculate a 2000 gallon fermentor containing 1200 gallons of the production medium of Example I. The fermentation was conducted at a temperature of 28° C. and an aeration rate of one volume of air per volume of broth per minute. After substantial antibiotic activity was obtained (approximately 48 to 72 hours), 1100 gallons of the whole fermentation broth, pH, 8.4, was extracted with approximately 350 gallons of methylisobutyl ketone. Concentration of the solvent extract in vacuo gave rise to an oily extract (1,190 grams) containing antibiotic Compounds 47,444, 47,985 and 48,039. Trituration with heptane (1×5.0 liters, 1×2.0 liters, 1×1.0 liter) then led to a viscous concentrate (241 grams) containing >95% of the antibiotic activity present in the starting extract of 1,190 grams.

The concentrate (241 grams) was dispersed on 500 grams of silica gel 60 (E. Merck, Darmstadt, Germany) in the presence of a liter of heptane and then added to a 2.0 liter sintered glass filter coated with 250 grams of silica gel 60. The silica gel was washed successively with a liter of heptane, 9 liters of chloroform, a liter of chloroform:ethyl acetate (9:1), a liter of chloroform:ethyl acetate (4:1), a liter of chloroform:ethyl acetate (7:3), a liter of chloroform:ethyl acetate (3:2), a liter of chloroform:ethyl acetate (1:1), a liter of chloroform:ethyl acetate (2.5:7.5) and 2.5 liters of ethyl acetate. All steps in the purification sequence were monitored by thin-layer chromatography. The greater part of the antibiotic activity was found in the last one liter of chloroform through the one liter of chloroform:ethyl acetate (1:1). These eluates were combined and evaporated in vacuo to an off-white foam (41 grams). The latter was dissolved in 400 ml of ethyl acetate and stirred for 30 minutes with 41 grams of Darco G60. Filtration followed by concentration in vacuo led to 36 grams of a white solid.

The minor, less polar antibiotic Compound 47,985 was found in the heptane and chloroform eluates (first two liters) whereas the minor, more polar antibiotic Compound 48,039 was found in the chloroform:ethyl acetate (3:2–2.5:7.5) eluates.

The material from charcoal treatment (36 grams in chloroform solution) was then added to the top of a silica gel 60 column (2"×96 cms) and developed with chloroform containing increasing amounts of ethyl acetate (20 ml cuts, chloroform (100%) - chloroform:ethyl acetate (50:50). Appropriate cuts from this column were combined to afford substantially pure Compound 47,444 (25.8 grams). An analytical sample of antibiotic Compound 47,444 was derived by further chromatography of an aliquot of the 25.8 gram sample (column dimensions 1"×92 cms) on silica gel $PF_{254}$ (E. Merck, Darmstadt, Germany) eluting with chloroform:ethyl acetate (1:1,v/v). All attempts to crystallize antibiotic Compound 47,444 were unsuccessful. It was obtained as an amorphous white solid.

The minor antibiotic Compounds 47,985 and 48,039 were present in such small amounts that it has not proved possible to isolate them in a state of homogeneity at this time.

Compound 47,444 (sample dried overnight in vacuo 45°–50° C.)

Elemental Analysis—C 64.40; H 7.61; N 2.56; O 25.43 (by difference).

Molecular Formula—$C_{28}H_{34}NO_8$ (M+515), high resolution mass spectrum. The $C^{13}$ nmr spectrum displays resonances consistent with the presence of 28 carbon atoms.

Optical Rotation—$[\alpha]_D = +49°$ (c=1.0, methanol).

Ultraviolet Absorption Maxima—$\lambda_{max}^{MeOH}$, 265 nm, $E_{1cm}^{1\%}$ 320.

Characteristic Infrared Bands (KBr disc) in microns as shown in FIG. 1: 2.90, 3.40, 5.76, 5.87, 6.40, 6.85, 7.05, 7.63, 8.53, 9.0, 10.58, 11.34 and 13.35.

Solubilities—Soluble in methanol, ethanol, chloroform, methylene chloride, acetone, methylisobutyl ketone and ethyl acetate. Insoluble in heptane and water.

What is claimed is:

1. An antibiotic mixture produced by cultivating *Nocardia argentinensis* Huang sp. nov. ATCC 31306 under submerged aerobic conditions in an aqueous nutrient medium containing an assimilable source of carbon and nitrogen until substantial antibiotic activity is obtained and separating said antibiotic mixture therefrom.

2. Antibiotic Compound 47,444 which is soluble in methanol, ethanol, chloroform, methylene chloride, acetone, methylisobutyl ketone and ethyl acetate; insoluble in heptane and water; has absorption maximum in methanol in the ultraviolet light region of the spectrum at 265 nm with $E_{1cm}^{1\%}$ value of 320; has the molecular formula of $C_{28}H_{37}NO_8$; has an optical rotation of $[\alpha]_D = +49°$ at a concentration of 1% in methanol; and when pelleted in KBr, exhibits characteristic absorption in the infrared region of the following wavelengths in microns: 2.90, 3.40, 5.76, 5.87, 6.40, 6.85, 7.05, 7.63, 8.53, 9.0, 10.58, 11.34 and 13.35.

3. A pharmaceutical composition suitable for combating Staphylococcal infections in animals comprising a pharmaceutically-acceptable carrier and a therapeutically-effective antistaphylococcal amount of Compound 47,444 as defined in claim 2.

* * * * *